United States Patent [19]

Shearer et al.

[11] Patent Number: 4,856,334

[45] Date of Patent: * Aug. 15, 1989

[54] BOND STRENGTH MEASUREMENT OF COMPOSITE PANEL PRODUCTS

[75] Inventors: Dwayne M. Shearer, Seattle; Richard C. Beetham, Enumclaw; Frank C. Beall, Puyallup, all of Wash.; John M. Rodgers, Sacramento, Calif.

[73] Assignee: Weyerhaeuser Company, Tacoma, Wash.

[ * ] Notice: The portion of the term of this patent subsequent to Jun. 14, 2005 has been disclaimed.

[21] Appl. No.: 172,719

[22] Filed: Apr. 6, 1988

Related U.S. Application Data

[63] Continuation-in-part of Ser. No. 53,929, May 26, 1987, Pat. No. 4,750,368.

[51] Int. Cl.⁴ ............................................. G01N 29/00
[52] U.S. Cl. ....................................... 73/588; 73/600;
 73/618; 73/639
[58] Field of Search ................ 73/588, 599, 600, 618,
 73/639, 643

[56] References Cited

U.S. PATENT DOCUMENTS

| | | | |
|---|---|---|---|
| 3,384,767 | 5/1968 | Arnold | 73/600 |
| 3,423,991 | 1/1969 | Collins | 73/618 |
| 3,780,570 | 12/1973 | Collins | 73/618 |
| 4,036,057 | 7/1977 | Morais | 73/88 |
| 4,073,007 | 2/1978 | Boivin | 73/627 |
| 4,201,093 | 5/1980 | Logan | 73/618 |
| 4,594,897 | 6/1986 | Bantz | 73/600 |
| 4,750,368 | 6/1988 | Shearer et al. | 73/618 |

OTHER PUBLICATIONS

J. Krautkramer et al., *Ultrasonic Testing of Materials* (Springer-Verlag, New York, 1983), pp. 293–296.
AET "Acoustic Emission Technology Corporation", Catalog, Jan. 1984.

*Primary Examiner*—John Chapman

[57] ABSTRACT

The invention is a method for the on-line nondestructive determination of the internal bond strength of composite panel products. The method involves impinging an ultrasound pulse against the panel by a first transducer and receiving a transmitted pulse at a second transducer. The received signal strength, temperature and panel thickness are entered into an algorithm from which the internal bond may be calculated. Preferably the receiving transducer is located on the opposite side of the panel and displaced somewhat from the first transducer. The inclusion of temperature and panel thickness as independent variables greatly improves the accuracy over that available from uncorrected ultrasound testing.

18 Claims, 4 Drawing Sheets

BOND STRENGTH MEASUREMENT OF COMPOSITE PANEL PRODUCTS

The present application is a continuation-in-part of Ser. No. 053,929, filed May 26, 1987, now U.S. Pat. No. 4,750,368.

BACKGROUND OF THE INVENTION

The present invention is a method for the on-line, nondestructive determination of the internal bond of composite panel products. The method is particularly useful as a process and quality control tool wherein it can give an immediate appraisal of the internal bond strength of products such as wood fiber, particle, flake, or strand boards. Measurements made shortly after pressing products of this type correlate well with conventional laboratory methods made several hours or days later.

For composite wood products such as those named above, internal bond strength and flexural strength are probably the two most important physical indicators of board quality. Flexural strength, sometimes termed modulus of rupture, is most indicative of surface strength while internal bond is more indicative of the interior or core strength of the product. In the past, it has been a matter of hours, or even days, before the results of quality control tests would be available to production personnel. This often resulted in large quantities of products being made which were outside quality specifications with nobody being aware of the problems.

In recent years equipment has been developed to attempt to nondestructively measure certain physical properties either on line during production or shortly thereafter. For example, Collins, in U.S. Pat. Nos. 3,423,991 and 3,780,570, shows systems using rolling transducers useful for determining voids or delamination in plywood. One transducer directs a pulse of ultrasonic energy against one face of the panel. An opposing transducer analyzes exponentially decaying reverberations to obtain the desired information. Other devices measure pulse propagation velocity as an indicator of the physical property being measured. One such device is shown in U.S. Pat. No. 4,073,007 to Boivin. Here the time for a pulse to travel a predetermined distance is sued as an indicator for measuring lack of planarity of a tensioned sheet metal strip. Logan, in U.S. Pat. No. 4,201,093, uses a rolling oil filled transducer to introduce ultrasonic signals into sheets.

A common feature of the Collins and Logan devices is the use of a transducer element contained within a rolling wheel or cylinder. Various means are used to couple energy from the transucer to the wheel and from there into the material being measured.

Devices of the types just described have achieved only limited use for a number of reasons. In many cases the reliability is very poor. In other cases, the device is unable to measure the desired physical property with sufficient accuracy and/or reliability. A system described in U.S. Pat. No. 4,036,057 to Morais has been used to determine adhesion or delamination in wood products and the tensile strength of graphite-epoxy composites. This uses an ultrasonic signal to propagate a stress wave through the material being tested. A receiving transducer detects the "ringdown" or decay of resonant waves produced within the substrate being tested. A device of the Morais type has been shown to give results having a general correlation with the internal bond strength of composite panel products such as particleboard. However, this correlation is so poor that is not usefully predictive for use as a quality control tool.

The present invention has overcome the problems experienced with prior art on-line testing devices and is capable of the accurate determination of the internal bond strength of numerous types of composite panel products.

SUMMARY OF THE INVENTION

The present invention is a method for on-line, nondestructive determination of the internal bond strength of composite panel products. The first step in the method is to measure the thickness of the product. Where the panels are of relatively uniform thickness, they may be assigned to a thickness class; e.g., 12–13 mm, 19–20 mm, etc. The consideration of thickness and temperature of the panels being measured has proved to be a critical and key improvement when used together with some of the prior ultrasonic techniques.

As the next step in the process, an ultrasound pulse is impinged against the panel through a first transducer which may or may not be in contact with the panel. This transmitted pulse is received by a second transducer spaced apart from the first transducer. This also either may or may not be in contact with the panel. The signal received by the second transducer is expressed as an output voltage. Then the thickness, panel surface temperature, and output signal voltage are entered into an equation of the form $IB = a + b(\text{output voltage}) + c(\text{temperature}) + d(\text{thickness}) + e(\text{thickness})^2$ The coefficients a, b, c, d and e can readily be determined experimentally for the particular equipment being used and product being tested. Finally, the equation is solved to give an estimate of the internal bond strength. This is most conveniently done using a dedicated microprocessor or computer which will give a visible readout or printout to a plant operator.

It will be readily evident that the particular order of the steps described is not critical. Thus, temperature and panel thickness could be measured following the ultrasound procedure.

In many cases the accuracy of the method is sufficient when, as noted before, the panels are simply assigned to a thickness class. In this case the second order equation just described can be simplified to a first order equation with the variables being only the second transducer output voltage and the panel temperature. In this case the equation has the following form $$IB = a + b(\text{output voltage}) + c(\text{temperature})$$

Here the coefficients a, b and c must be determined for each individual thickness class being tested.

It is an object of the present invention to provide a method for the accurate nondestructive determination of the internal bond of composite wood panels.

It is another object to provide a method for on-line determination of the internal bond of particleboard at or near the point of press discharge.

It is a further object to provide a method for on-line determination of internal bond in composite panels that is not subject to the inaccuracies inherent in related prior art methods.

These and many other objects will become readily apparent to those skilled in the art upon reading the following detailed description taken in conjunction with the drawings.

DETAILED DESCRIPTION OF THE PREFERRED EMBODIMENT

Figure 1:
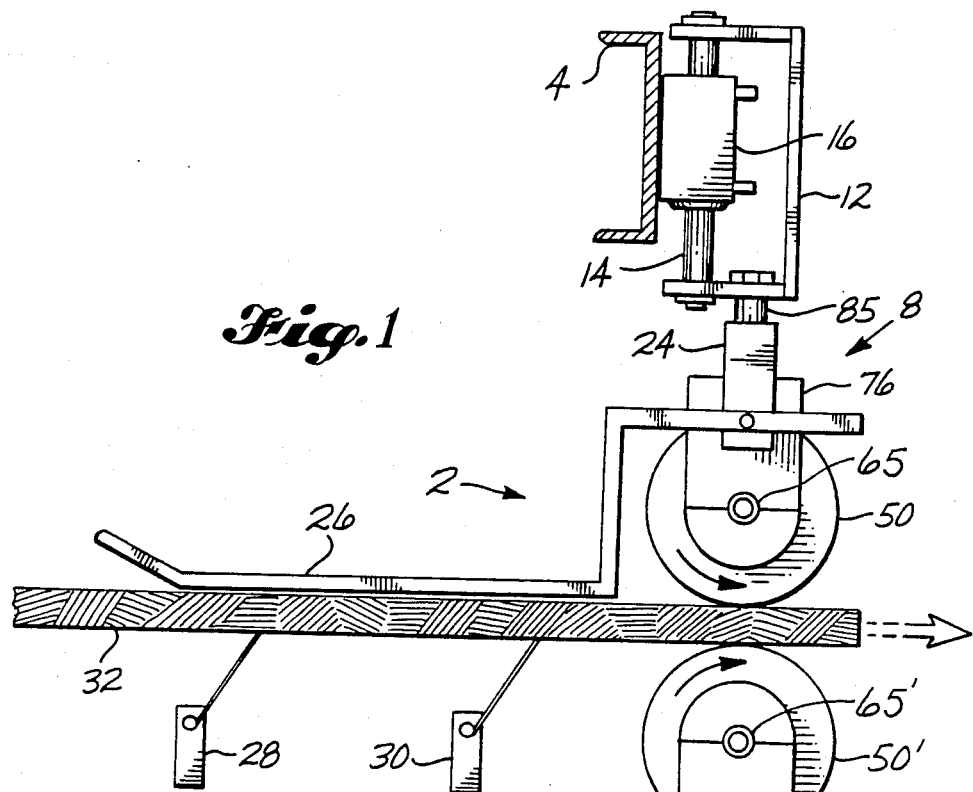
FIG. 1 is a side elevation view of key mechanical components of the testing apparatus.

The apparatus used with the present method is conventional and, for the most part, can be assembled from components which are commercially available. FIG. 1 shows a typical measurement setup as it might be used in a panel manufacturing operation, such as a particleboard mill. The testing apparatus, generally shown at 2, has frame members 4, 6 on which are mounted respectively an upper transducer wheel assembly 8 and lower transducer wheel assembly 10. The upper assembly has a subframe 12 which is mounted to both ends of a piston rod 14 in a double acting cylinder 16. An upper yoke 24 is mounted to subframe 12 by a shouldered bolt or similar mounting means 85. Mounted within yoke 76 on axle 65 is a rolling transducer 50. The lower rolling transducer assembly 10 is constructed in somewhat similar fashion with a support rod 18 holding subframe 20. The support rod is journaled in a bushing 22 where, in this embodiment, it is free to have limited rotation but fixed so that it will not translate up or down. Mounting member 85', which may also be a shouldered bolt, holds the lower yoke assembly 76' on which the lower rolling transducer assembly 50' is mounted on axle 65'.

An arm 26 is mounted on upper yoke 24 to detect the presence of overlapped panels which might damage the instrument. The shorter end of arm 26 is connected to a sensor mechanism, not shown, which will cause upper transducer assembly 8 to be withdrawn if overlapped panels are present.

The upper rolling transducer assembly 8 is normally raised out of the line of contact when no panels are passing. An approaching panel will contact presence/absence detectors 28, 30 and signal a control mechanism, not shown, to lower assembly 8 into contact with panel 32 after it is in position over lower transducer assembly 10. In similar fashion, when the trailing end of the panel clears switches 28, 30, transducer assembly 8 is raised before the panel has completely passed the rolling transducers. This eliminates impact damage to the upper transducer assembly where it might otherwise be hit by the leading edge of a panel or dropped as it leaves the trailing edge.

Two features of the invention are associated with the apparatus shown in FIG. 1 but are not illustrated here. One of these is an optional panel thickness detector and the other is a panel temperature sensor. If a thickness detector is used, it may be either a contact type or a noncontact type, for example, a precision sonar surface location indicator.

Panel temperature may be measured or suitably estimated in a number of ways. It is the interior temperature of the panel which is important to the present invention. This may be closely estimated from surface temperature in most cases. For surface temperature detection a number of commercially available infrared measuring devices may be used. One which has proved satisfactory is the Optitherm Series 12-8500, available from Pyrometer Instrument Company, Northvale, New Jersey. Another method of temperature estimation is based on a knowledge of the time that the panels have been out of the hot press upstream from the measuring position. The temperature within the press can be determined with acceptable accuracy as can the rate of heat loss as the panels move down the conveyor line. If the time between ejection from the press and measurement can be sufficiently well controlled, no temperature measurement instrumentation is required.

Figure 2:
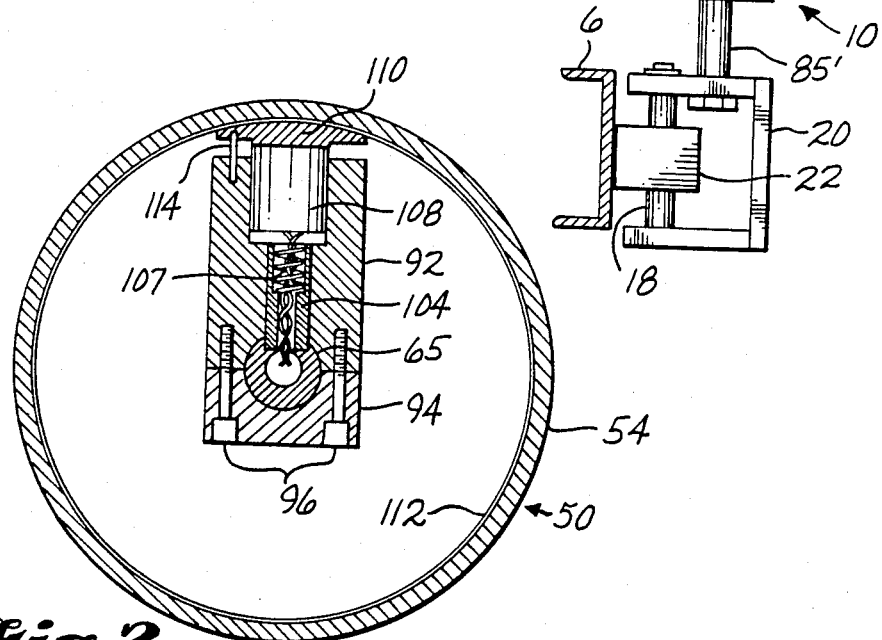
FIG. 2 shows the interior detail of a suitable rotary transducer.

A rolling transducer assembly suitable for use with the present method is shown in FIG. 2. This has a metallic rim 54 with face plates, not shown, mounted on each side and journaled about shaft 65. A transducer mount 92, 94 is connected within the rim and clamped in fixed position on shaft 65 by cap screws 96. Within the transducer mount is a sleeve 104 containing a spring or other resilient member 107 acting against a piezo electric transducer 108. Directly connected to the transducer is a rim contacting shoe 110 which floats on a thin oil film 112. A guide pin 114 may be necessary to help retain shoe 110 in its desired position. The lead wires from transducer 108 are brought out through an interior bore hole in shaft 65.

Figure 3:
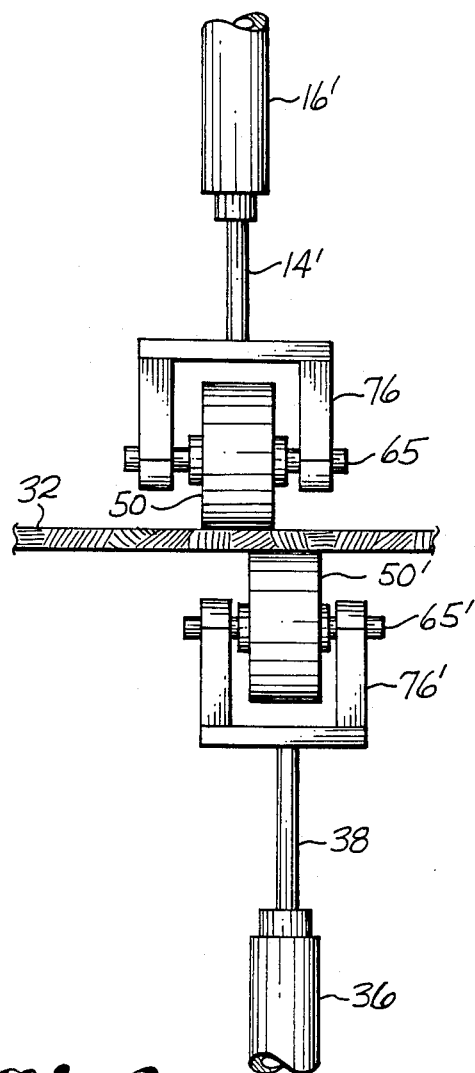
FIG. 3 is an end elevation view showing the arrangement of the upper and lower transducers.

An alternative representation of the apparatus is seen in FIG. 3, which is shown as an end-on elevation corresponding to the side elevation of FIG. 1. The mounting of yoke 76 is simplified as shown here and it is located on piston rod 14' depending from cylinder 16'. In similar fashion, the lower rolling transducer assembly is shown with yoke 76' mounted on piston rod 38 of cylinder 36. It is acceptable for the two transducers to have contact points with the panel directly above each other. Stated otherwise the transducers may be located along a common axis. However, it is desirable that they be displaced somewhat in order to sample a larger portion of the panel being tested. The amount of displacement is a compromise between increased accuracy on the one hand and greater signal attenuation of the other. Any displacement between the two transducers may be either lateral, as shown in FIG. 3, or it may be longitudinal. While in some cases the transducers may be located on the same side of the panel, it is preferably that they be located on opposite sides so that the pulse is transmitted through the entire thickness of the panel.

Figure 4:
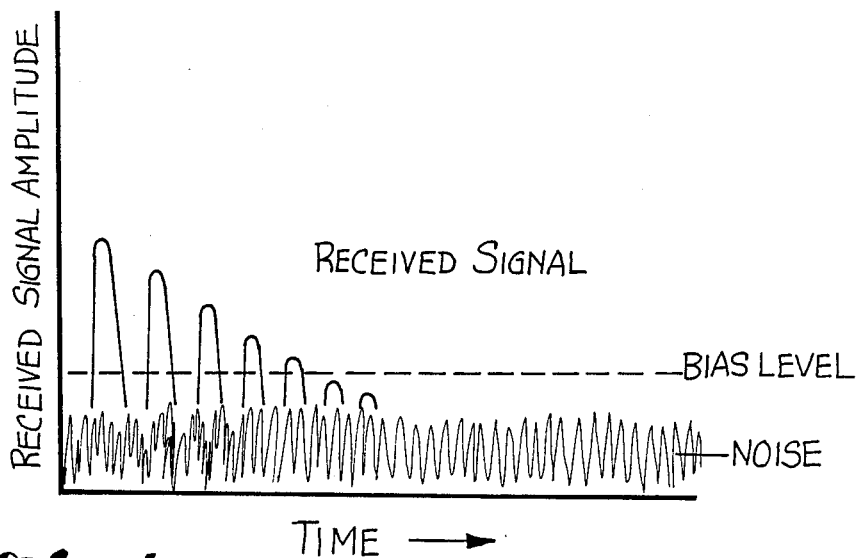
FIG. 4 is a graph showing the measurement of ringdown count.

Suitable acoustic emission equipment for use with the present apparatus is available from a number of suppliers. One type of equipment that has proved suitable is an instrument designated Model 302, available from Acoustic Emission Technology Corporation, Sacramento, California. The acoustic driver directs an ultrasonic pulse against the panel. The received signal may be processed in one of two ways. In the first, the average RMS voltage produced in response to the transmitted pulse is measured. In the other, the ringdown count of the oscillations produced in response to the transmitted pulse is measured. Preferably, when this latter method is employed, the system is biased, as shown in FIG. 4, so that only those pulses having as greater amplitude than the bias level are counted. In this way the bias level can be set above the ambient noise level of the system to achieve greater accuracy. A gating circuit may be used when RMS voltage received signals are being processed. This permits examination of signals for some discrete time period after each driver pulse and can reduce the contribution of spurious noise.

Figure 5:
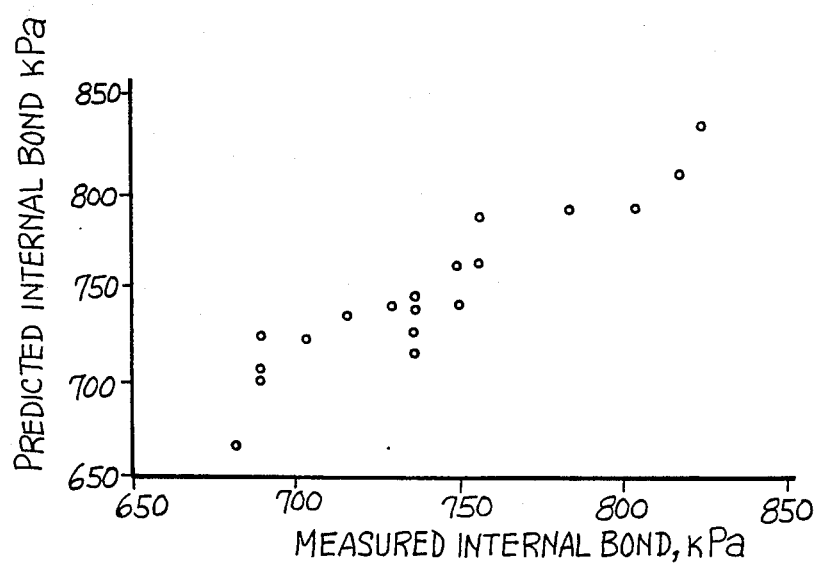
FIG. 5 is a graph showing the predicted internal bond from online measurement compared with internal bond of the same panels measured in the laboratory.

FIG. 5 is a plot of 18 samples in which predicted internal bond from on-line measurement is compared with later laboratory tests of internal bond. The samples shown in this graph were measured between the temperature extremes of 40° C. and 105° C. on a 5/8 inch premium quality particleboard. The correlation, as shown by the statistical value $R^2$, was 0.85. When a similar set of measurements was attempted in which the ringdown voltage alone was considered, ignoring temperature, the value $R^2$ was only 0.4. In essence, under these conditions no correlation existed and there was a high probability that any perceived relationship between on-line and laboratory values was due entirely to chance. In the data collected for the graph shown in FIG. 5, the panels were of sufficiently uniform thickness so that this component could be ignored in the algorithm used for calculation of internal bond. In this system the coefficients were as follows:

$$IB = -0.3 + 40.9(\text{ringdown voltage}) + 0.26(\text{temperature})$$ with internal bond expressed in $lb/in^2$ and temperature in ° C. The values determined by this algorithm have been multiplied by a factor of 6.89 to convert them to kilopascals as illustrated on the graph.

Figure 6:
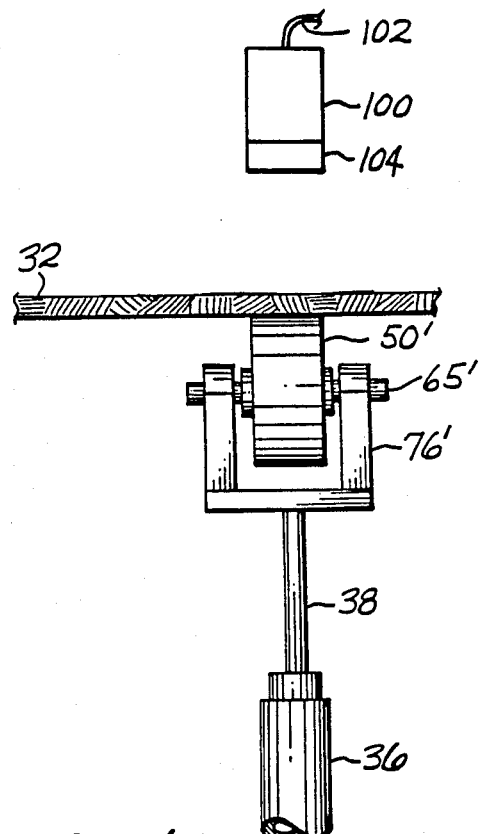
FIGS. 6 and 7 are end elevation views, similar to FIG. 3, showing alternative transducer type and positioning arrangements.
Figure 7:
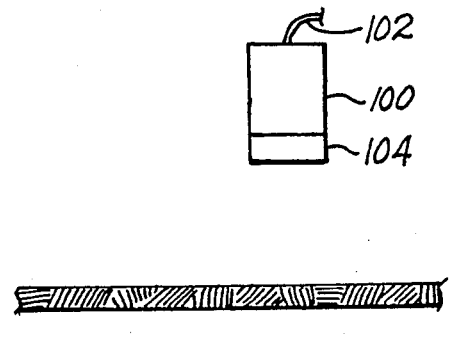
Figure 7:
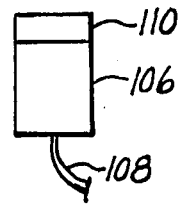

While the best currently available technology would suggest the use of rolling transducers in physical contact with the panels being measured, this is not essential for achieving satisfactory results. Noncontacting ultrasonic transmitting and receiving transducers with sufficient power and senstitivy are presently available for use. A noncontact-type transmitting transducer may be used with either a contacting or noncontacting receiving transducer. Similarly, a contacting transmitter may be used with a contacting or noncontacting receiving transducer. FIGS. 6 and 7 are typical of these arrangements. Here an air coupled ultrasonic transmitter 100 is located above the panel 32 being measured. This is connected to an acoustic driver as described earlier by cable 102. Preferably a conventional impedance coupling device 104 is used to minimize signal loss at the air/transmitter interface. The rolling receiver 50 is also as described earlier.

In FIG. 7 an air coupled receiving transducer 106 is also displaced from panel 32 an appropriate distance. This is connected by cable 108 to the receiver circuitry associated with the driver unit. The receiving transducer may be of any suitable type; e.g., one based on a piezoceramic crystal or one based on piezoelectric film such a polyvinyl flouride.

As with the arrangement using two panel contacting rolling transducers, a frequency in the range of about 50–100 khz appears to give the best results.

The transmitting transducer 100 is preferably a piezoceramic crystal using conventional "tone burst" technology to drive the unit at its natural resonant frequency and increase output signal strength.

Having thus described the best mode presently known to the inventor of practicing the present invention, it will become readily apparent to those skilled in the art that many variations can be made in the procedures described without departing from the spirit of the invention. The invention is considered to be limited only as it is defined in the following claims.

We claim:

1. A method for the on-line, nondestructive determination of the internal bond strength of composite panel products which comprises:
   designating a thickness class for the panels being measured;
   determining the temperature of the panel;
   impinging an ultrasound pulse against the panel through a first transducer;
   receiving the transmitted pulse at a second transducer spaced apart from the first transducer;
   expressing the received signal as an output voltage;
   entering temperature and output signal voltage into a linear equation of the form $$IB = a + b(\text{output voltage}) + c(\text{temperature})$$

where the coefficients are determined for the given thickness class; and
   solving the equation to determine the internal bond strength.

2. The method of claim 1 wherein the panel product is a composite wood panel.

3. The method of claim 1 where the output of the second transducer is the average RMS voltage produced in response to the transmitted pulse.

4. The method of claim 1 where the output of the second transducer is a voltage analog of the ringdown count of the oscillations produced in response to the transmitted pulse.

5. The method of claim 4 in which the ringdown count is measured above a bias level set greater than the ambient noise level.

6. The method of claim 1 in which the second transducer is located on the opposite side of the panel from the first transducer.

7. The method of claim 6 in which the second transducer is linearly displaced either transversely or longitudinally from the first transducer.

8. The method of claim 1 wherein the first transducer is spaced apart from the panel.

9. The method of claim 1 wherein the first and second transducers are spaced apart from the panel.

10. A method for the on-line, nondestructive determination of the internal bond strength of composite panel products which comprises:
    measuring the thickness of the panel;
    determining the temperature of the panel;
    impinging an ultrasound pulse against the panel through a first transducer;
    receiving the transmitted pulse at a second transducer spaced apart from the first transducer;
    expressing the received signal as an output voltage;
    entering the thickness, temperature, and output signal voltage into an equation of the form $$IB = a + b(\text{output voltage}) + c(\text{temperature}) + d(\text{thickness}) + e(\text{thickness})^2;$$

and solving the equation to determine the internal bond strength.

11. The method of claim 10 wherein the panel product is a composite wood panel.

12. The method of claim 10 where the output of the second transducer is the average RMS voltage produced in response to the transmitted pulse.

13. The method of claim 10 where the output of the second transducer is a voltage analog of the ringdown count of the oscillations produced in response to the transmitted pulse.

14. The method of claim 13 in which the ringdown count is measured above a bias level set greater than the ambient noise level.

15. The method of claim 10 in which the second transducer is located on the opposite side of the panel from the first transducer.

16. The method of claim 15 in which the second transducer is linearly displaced either transversely or longitudinally from the first transducer.

17. The method of claim 10 wherein the first transducer is spaced apart from the panel.

18. The method of claim 10 wherein the first and second transducers are spaced apart from the panel.

* * * * *

UNITED STATES PATENT AND TRADEMARK OFFICE
CERTIFICATE OF CORRECTION

PATENT NO. : 4,856,334

DATED : Aug. 15, 1989

INVENTOR(S) : Shearer et al.

It is certified that error appears in the above-identified patent and that said Letters Patent is hereby corrected as shown below:

On the title page

[75]  Inventors: Dwayne M. Shearer, Seattle; Richard C. Beetham, Enumclaw; Frank C. Beall, Puyallup, all of Wash.; John M. Rodgers, Sacramento, Calif. should read - -- Dwayne M. Shearer, Seattle; Richard C. Beetham, Enumclaw; Frank C. Beall, Puyallup, all of Wash. --

Signed and Sealed this

Ninth Day of October, 1990

Attest:

HARRY F. MANBECK, JR.

*Attesting Officer*  *Commissioner of Patents and Trademarks*